(12) United States Patent
Dugar et al.

(10) Patent No.: US 10,752,589 B2
(45) Date of Patent: Aug. 25, 2020

(54) TRIGONELLINE BASED COMPOUNDS

(71) Applicant: SPHAERA PHARMA PVT. LTD., Manesar (IN)

(72) Inventors: Sundeep Dugar, Manesar (IN); Dinesh Mahajan, Punjab (IN); Somdutta Sen, Manesar (IN)

(73) Assignee: SPHAERA PHARMA PVT. LTD., Manesar (IN)

( * ) Notice: Subject to any disclaimer, the term of this patent is extended or adjusted under 35 U.S.C. 154(b) by 0 days.

(21) Appl. No.: 16/085,125

(22) PCT Filed: Mar. 14, 2017

(86) PCT No.: PCT/IN2017/050091
§ 371 (c)(1),
(2) Date: Sep. 14, 2018

(87) PCT Pub. No.: WO2017/158621
PCT Pub. Date: Sep. 21, 2017

(65) Prior Publication Data
US 2019/0077757 A1      Mar. 14, 2019

(30) Foreign Application Priority Data
Mar. 14, 2016   (IN) ............................ 2882/DEL/2015

(51) Int. Cl.
| | | |
|---|---|---|
| *C07D 213/80* | (2006.01) | |
| *C07D 213/02* | (2006.01) | |
| *C07D 401/14* | (2006.01) | |
| *C07D 405/14* | (2006.01) | |
| *C07D 405/12* | (2006.01) | |
| *C07D 471/14* | (2006.01) | |
| *C07D 401/12* | (2006.01) | |
| *C07D 407/14* | (2006.01) | |
| *A61K 31/337* | (2006.01) | |

(52) U.S. Cl.
CPC ......... *C07D 213/02* (2013.01); *C07D 213/80* (2013.01); *C07D 401/12* (2013.01); *C07D 401/14* (2013.01); *C07D 405/12* (2013.01); *C07D 405/14* (2013.01); *C07D 407/14* (2013.01); *C07D 471/14* (2013.01); *A61K 31/337* (2013.01)

(58) Field of Classification Search
CPC .. C07D 213/02; C07D 213/80; C07D 407/14; C07D 401/12; C07D 401/14; C07D 471/14; C07D 405/12; C07D 405/14; A61K 31/337

USPC ........................................................ 546/347
See application file for complete search history.

(56) References Cited

U.S. PATENT DOCUMENTS

| | | | |
|---|---|---|---|
| 5,411,984 A | 5/1995 | Kingston et al. | |
| 6,559,164 B1 | 5/2003 | Fotouhi et al. | |
| 2015/0118294 A1* | 4/2015 | Song .................... | A61K 31/455 424/452 |
| 2015/0252027 A1* | 9/2015 | Dugar .................. | C07D 401/14 540/495 |

FOREIGN PATENT DOCUMENTS

| | | |
|---|---|---|
| EP | 1336602 | 8/2003 |
| EP | 2423215 | 2/2012 |
| RU | 2565450 C1 * | 10/2015 |
| WO | 1992004038 | 12/1992 |
| WO | 1997/15571 | 5/1997 |
| WO | 1997015571 | 5/1997 |
| WO | WO 2014/162320 A2 * | 10/2014 |
| WO | WO 2015/023593 A1 * | 2/2015 |
| WO | WO 2015/095819 A2 * | 6/2015 |

OTHER PUBLICATIONS

Holland et al, Direct Reaction of Amides with Nitric Oxide To Form Diazeniumdiolates, The Journal of Organic Chemistry, 2014, 79(19), p. 9389-9393 (Year: 2014).*
Lee et al. Potential mitochondrial isocitrate dehydrogenase R1400 mutant inhibitor from trastional Chinese medicine against cancers, Biomed Research International, 2014, p. 11 (Year: 2014).*
International Search Report for PCT Application PCT/IN2017/050091 dated Jul. 24, 2017, pp. 1-3.
Abdu-Allah H., et al, "Synthesis of trigonelline and nicotinamide linked prodrugs of 5-aminosalicylic acid (5-ASA) with analgesic and anti-inflammatory effects", Bull. Pharm. Sci., Assiut University, vol. 28, Issue 2, pp. 237-253 (2005).

(Continued)

*Primary Examiner* — Taylor V Oh
(74) *Attorney, Agent, or Firm* — Timothy H. Van Dyke; Beusse, Wolter, Sanks & Maier PLLC

(57) ABSTRACT

The present invention provides novel compounds with improved solubility and altered pharmacokinetic properties. The compounds of the present invention may be represented by Formula (I).

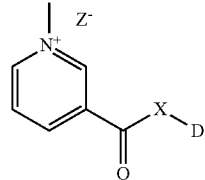

Formula (I)

2 Claims, No Drawings

(56) References Cited

OTHER PUBLICATIONS

Nicolaou, K.C. et al., "Chemical synthesis and biological evaluation of C-2 taxoids", Mar. 8, 1995, Journal of the American Chemical Society, vol. 117, No. 9, pp. 2409-2420.
Guthrie, David B. et al., "Water-Solule Progesterone Analogues are Effective, Injectable Treatments in Animal Models of Traumatic Brain Injury", May 10, 2012, ACS Medicinal Chemistry Letters, vol. 3, No. 5, pp. 362-366.
EP Application No. 17766001.6; EP Search Report, dated Jul. 31, 2019, 11 pages.
Guthrie, David B. et al., "Water-Soluble Progesterone Analogues Are Effective, Injectable Treatments in Animal Models of Traumatic Brain Injury", ACS Med. Chem. Lett, 2012, vol. 3, pp. 362-366.
Nicolaou, K.C. et al., "Chemical Synthesis and Biological Evaluation of C-2 Taxoids", J. Am. Chem. Soc, 1995, vol. 117, pp. 2409-2420.
EP17766001.6; European Extended Search Report, dated Nov. 11, 2019, 9 pages.

\* cited by examiner

TRIGONELLINE BASED COMPOUNDS

FIELD OF INVENTION

The present invention relates to novel compounds with improved solubility and altered pharmacokinetic properties and a method for altering the pharmacokinetic profile of a compound.

BACKGROUND OF THE INVENTION

Many compounds of pharmaceutical interest face challenges during the process of drug development because of their pharmacokinetic or pharmacodynamic properties and also due to their poor solubility.

Molecular modifications of a drug substance are designed to enhance, amongst other aspects, the specificity for a particular target site, increasing its potency, improving its rate and extent of absorption, modifying the time span in which the drug becomes bio-available in the body while preserving the efficacy and toxicity value of the drug. There are limited number of chemical modifications known which can enhance aqueous solubility of the drug substance independent of pH or which can alter the pharmacokinetic properties of drugs without affecting its efficacy and toxicity.

It is interesting to note that, attempts to improve solubility of pharmaceutical compounds such as taxanes based on molecular modification have not resulted in any successful clinical products. Certain prodrugs of Taxol have been prepared which are purported to undergo in vivo transformation into Taxol and some other product. For instance, PCT patent publication no. WO 1997044063 discloses certain prodrugs but appears that these compounds still do not have the desired pharmacokinetic properties. Pharmaceutical industry majorly depends on novel formulations or excipients to generate a desirable solubility profile for molecules of biological interest to develop them for clinical use.

Some alkaloids having a purine or pyrimidine base type structures have been known in the prior art for the molecular modification of drug species for site specific drug delivery.

For instance, EP0110955 B1 discloses a compound of Formula [D-DHC] for the site specific/sustained delivery of a centrally acting drug species to the brain. The compound on administration gets converted to quaternized salt inside the body where it is locked inside the brain only and the salt entering other parts of the body gets excreted readily from liver and kidney. Thus, the concentration of quaternary salt is higher in brain as compared to the other parts of the body.

There is still a need to develop better prodrugs or modified compounds having improved solubility and/or pharmacokinetic properties for the effective drug delivery without loss of therapeutic efficacy and increase in toxicity of active molecule or drug.

OBJECT OF THE INVENTION

An object of the invention is to provide novel compounds with better aqueous solubility independent of pH of the media and improved or altered pharmacokinetic profile by a chemical modification using trigonelline as derivatizing agent,

SUMMARY OF THE INVENTION

The present invention provides novel compounds with improved solubility and altered pharmacokinetic properties. The compounds of the present invention may be represented by Formula I as below:

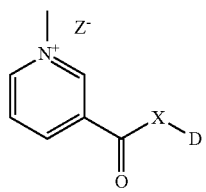

Formula I wherein DX— is an active pharmaceutical ingredient (API) or a drug substance and;

X is either O, or NR; or a functionalizable N which is a part of the API or drug substance.

Z is selected from Cl—, Br—, I—, mesylate, tosylate, tetrafluoroborate, or phosphate.

R is H, $CH_3$, lower straight chain or branched chain alykyl; alternatively X can also be part of a 3-7 membered ring when there is a bond present between R and another atom on D.

The present invention also discloses a process of preparing the compounds of the present invention and use of the compounds of the present invention and the compound of formula I is not substrate for CYP450.

DETAILED DESCRIPTION OF THE INVENTION

Accordingly, the present invention provides a novel compound with improved solubility and altered pharmacokinetic properties and a method for altering the pharmacokinetic profile of a compound.

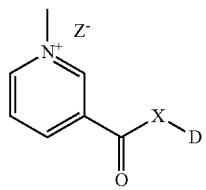

Formula I wherein DX— is an active pharmaceutical ingredient (API) or a drug substance and;

X is either O, or NR, or a functionalizable N which is a part of the API or drug substance;

Z is selected from Cl—, Br—, I—, mesylate, tosylate, tetrafluoroborate, or phosphate.

R is H, $CH_3$, lower straight chain or branched chain alkyl; alternatively X can also be part of a 3-7 membered ring when there is a bond present between R and another atom on D.

The active pharmaceutical ingredient (API) or drug substance may be selected from the group of analgesic agents; anesthetic agents; antiarthritic agents; respiratory drugs, including antiasthmatic agents; anticancer agents, including antineoplastic agents; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; alpha adrenergic antagonists or agonists; cough and cold preparations, including decongestants; antitussives; diuretics; gastrointestinal (GI) motility agents; hormones; hormonolytics; hypnotics; hypoglycemic agents; immunosuppressive agents; leukotriene inhibitors; mitotic inhibitors; phosphodiesterase inhibitors; muscle relaxants; narcotic antagonists; opiod modulators; nicotine; nictone/acetylcholine antagonists or agonists; psychostimulants; sedatives; steroids; tranquilizers; and vasodilators including general coronary, peripheral and cerebral.

The active pharmaceutical ingredient (API) or drug substance may preferably be selected from the group of anticancer compounds such as paclitaxel, docetaxel and cabazitaxel; phosphodiestrase 5 inhibitors such as tadalafil; vasodilators such as dopamine; narcotic antagonists; opiod modulators; nicotine; nictone/acetylcholine antagonists or agonists; most preferably the active pharmaceutical ingredient is an anticancer compound.

The present invention discloses compounds of Formula II and Formula III;

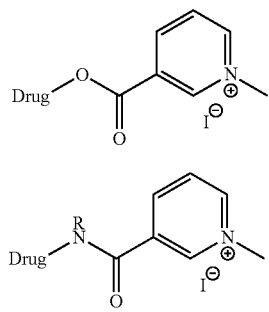

Formula (II)

Formula (III)

Wherein the drug may be any active pharmaceutical compound or drug substance as mentioned above.

The compound of the Formula (II) may be obtained when the active pharmaceutical ingredient or the drug substance is attached to the compound of Formula (IV) through a functionalizable oxygen such as hydroxyl of the active pharmaceutical ingredient or the drug substance by using standard coupling methods for a hydroxyl and an acid.

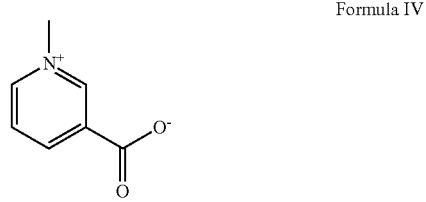

Formula IV

The compound of the Formula (III) may be obtained when the active pharmaceutical ingredient or the drug substance is attached to the compound of Formula (IV) through a functionalizable nitrogen such as amino group of the active pharmaceutical ingredient or the drug substance by using standard coupling methods for a hydroxyl and an acid.

The present invention also includes various compounds that fall within the scope of the compound of formula (I). A compound of formula I is not substrate for CYP450.

The compounds of formula (I) are illustrated herein below at Table 1. Table 1, shows an exemplary but a non-limiting list of currently existing active pharmaceutical agents or drug substances that can be modified using the methods described in this invention.

TABLE 1

Illustrative compounds of the present invention

| Compound no. | Structure/Name | IUPAC nomenclature |
|---|---|---|
| 1001 | | 3-((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium iodide |

TABLE 1-continued

Illustrative compounds of the present invention

| Compound no. | Structure/Name | IUPAC nomenclature |
|---|---|---|
| 1002 | | 3-((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Mesylate |
| 1003 | | 3-((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tetrafluoroborate |
| 1004 | | 3-((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tosylate |

TABLE 1-continued

Illustrative compounds of the present invention

| Compound no. | Structure/Name | IUPAC nomenclature |
|---|---|---|
| 1005 | | 3-((6R,12aR)-6-(benzo[d][1,3]dioxol-5-yl)-2-methyl-1,4-dioxo-1,2,3,4,6,7,12,12a-octahydropyrazino[1',2':1,6]pyrido[3,4-b]indole-7-carbonyl)-1-methylpyridin-1-ium iodide; |
| 1006 | | 3-((4-((1E,4Z,6E)-5-hydroxy-7-(4-hydroxy-3-methoxyphenyl)-3-oxohepta-1,4,6-trien-1-yl)-2-methoxyphenoxy)carbonyl)-1-methylpyridin-1-ium iodide |
| 1007 | | 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-methylpyridin-1-ium) iodide |
| 1008 | | 3-(((((2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl)oxy)carbonyl)-1-methylpyridin-1-ium iodide |

TABLE 1-continued

Illustrative compounds of the present invention

| Compound no. | Structure/Name | IUPAC nomenclature |
|---|---|---|
| 1009 | | 3-((1-((2R,4R,5R)-3,3-difluoro-4-hydroxy-5-(hydroxymethyl)tetrahydrofuran-2-yl)-2-oxo-1,2-dihydropyrimidin-4-yl)carbamoyl)-1-methylpyridin-1-ium iodide |
| 1010 | | 3-((((2R,3R,5R)-5-(4-amino-2-oxopyrimidin-1(2H)-yl)-4,4-difluoro-2-(hydroxymethyl)tetrahydrofuran-3-yl)oxy)carbonyl)-1-methylpyridin-1-ium iodide |
| 1011 | | 3-((R)-2-((S)-(2,8-bis(trifluoromethyl)quinolin-4 yl)(hydroxy)methyl)piperidine-1-carbonyl)-1-methylpyridin-1-ium |
| 1012 | | (R)-3-(((1-(4-((2-(5-chloro-2-fluorophenyl)-5-isopropylpyrimidin-4-yl)amino)nicotinamido)propan-2-yl)oxy)carbonyl)-1-methylpyridin-1-ium |

TABLE 1-continued

Illustrative compounds of the present invention

| Compound no. | Structure/Name | IUPAC nomenclature |
|---|---|---|
| 1013 | | (S)-3-(((1-(4-((2-(5-chloro-2-fluorophenyl)-5-isopropylpyrimidin-4-yl)amino)nicotinamido)propan-2-yl)oxy)carbonyl)-1-methylpyridin-1-ium iodide |

The compounds of the present invention include but are not limited to:

i. 3-(((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium iodide;

ii. 3-(((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Mesylate;

iii. 3-(((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tetrafluoroborate;

iv. 3-(((((1R,2R)-1-benzamido-3-(((2aR,4S,6R,9S,11S,12S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tosylate;

v. 3-((6R,12aR)-6-(benzo[d][1,3]dioxol-5-yl)-2-methyl-1,4-dioxo-1,2,3,4,6,7,12,12a-octahydropyrazino[1',2':1,6]pyrido[3,4-b]indole-7-carbonyl)-1-methylpyridin-1-ium iodide;

vi. 3-((4-((1E,4Z,6E)-5-hydroxy-7-(4-hydroxy-3-methoxyphenyl)-3-oxohepta-1,4,6-trien-1-yl)-2-methoxyphenoxy)carbonyl)-1-methylpyridin-1-ium iodide;

vii. 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-methylpyridin-1-ium) iodide;

viii. 3-(((((2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl)oxy)carbonyl)-1-methylpyridin-1-ium iodide;

ix. 3-((1-((2R,4R,5R)-3,3-difluoro-4-hydroxy-5-(hydroxymethyl)tetrahydrofuran-2-yl)-2-oxo-1,2-dihydropyrimidin-4-yl)carbamoyl)-1-methylpyridin-1-ium iodide;

x. 3-(((((2R,3R,5R)-5-(4-amino-2-oxopyrimidin-1(2H)-yl)-4,4-difluoro-2-(hydroxymethyl)tetrahydrofuran-3-yl)oxy)carbonyl)-1-methylpyridin-1-ium iodide.

xi. 3-((R)-2((S)-(2,8-bis(trifluoromethyl)quinolin-4 yl)(hydroxy)methyl) piperidine-1-carbonyl)-1-methylpyridin-1-ium xii. (R)-3-(((1-(4-((2-(5-chloro-2-fluorophenyl)-5-isopropylpyrimidin-4-yl)amino)nicotinamido)propan-2-yl)oxy)carbonyl)-1-methylpyridin-1-ium xiii. (S)-3-(((1-(4-((2-(5-chloro-2-fluorophenyl)-5-isopropylpyrimidin-4-yl)amino)nicotinamido)propan-2-yl)oxy)carbonyl)-1-methylpyridin-1-ium iodide In an aspect, the present invention includes compound of formula I, which may be represented by formula V;

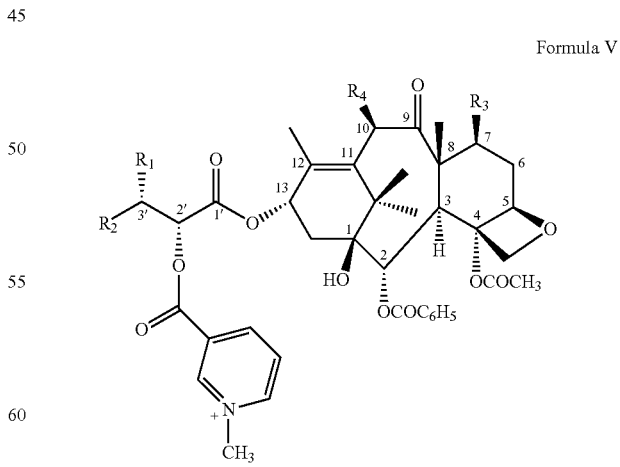

Formula V wherein $R_1$ is selected from an cyclic or acyclic or branched alkyl, aryl such as methyl, propyl, isopropyl, n-butyl, t-butyl or aralkyl such as benzyl, hydrogen, tertbutoxycarbonylamino or N-phenylcarbamoyl;

$R_2$ is selected from hydrogen, hydroxyl, acyclic, cyclic or branched alkyl, aryl or an aralkyl group;

$R_3$ and $R_4$ are independently selected from the group of hydrogen, hydroxyl, lower alkyl, lower alkoxy, acetyl or benzyl.

The present invention also discloses process for preparing the compound of Formula (I). The compound of formula (I) may be prepared by the following general schemes described herein below:

The method of preparing the compound of formula (I) may be based on the functional group of the active pharmaceutical ingredient or the drug substance.

For instance for active pharmaceutical ingredient or the drug substances containing hydroxyl as the functional group may be prepared following the synthetic Scheme for 2 as set out herein below:

General Synthetic Scheme of Modification of Drugs or Molecules of Biological Interests Having —OH as One of the Functional Group.

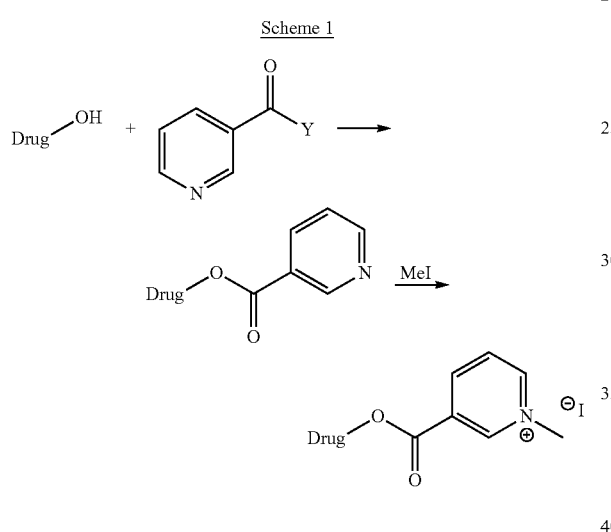

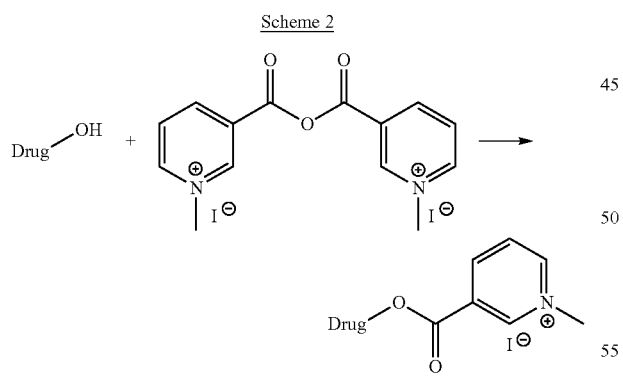

wherein Y is selected from the group comprising OH, Cl, F, Br or any activated form of acid such as anhydride;

Wherein the drug may be any active pharmaceutical compound or drug substance as mentioned above.

The present invention also discloses a process for synthesis of compounds of formula (I), wherein the functional group of the active ingredient is —NH—.

For instance, the compounds containing amino group as the functional group may be prepared the synthetic scheme 3 or 4 as set out herein below:

General Synthetic Scheme of Modification of Drugs or Molecules of Biological Interests Having —NH— as One of the Functional Group.

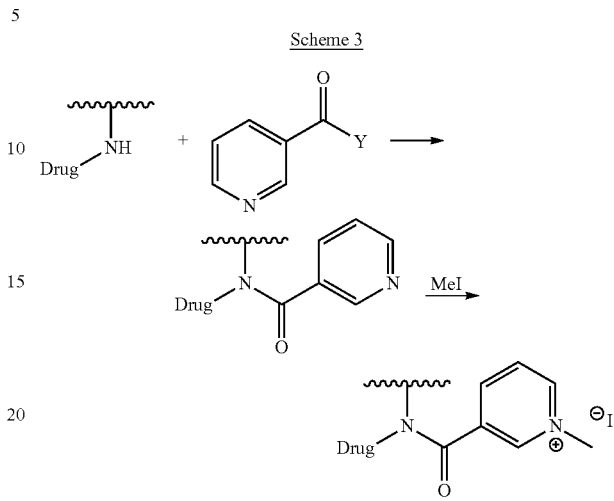

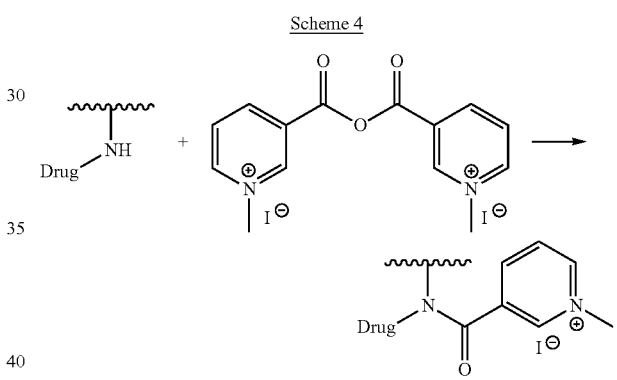

wherein Y is selected from the group comprising OH, Cl, F, Br or any activated form of acid such as anhydride;

Wherein the drug may be any active pharmaceutical compound or drug substance as mentioned above.

The Synthesis of compounds of formula I may consist of the following steps;

Step 1:

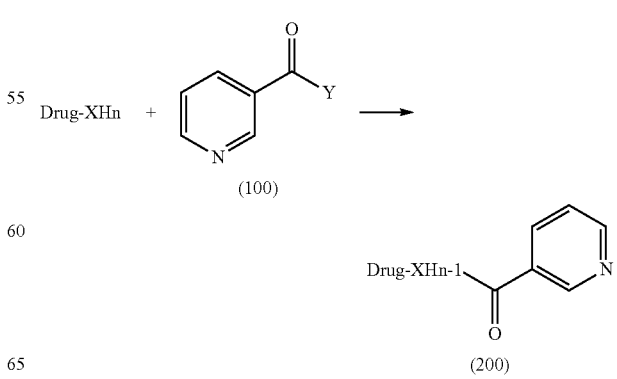

wherein Y is selected from halides such as F, Cl or Br, and OH and X is selected from O, N, and, n=0 to 2 depending on the allowable valency of X. The active pharmaceutical ingredient is dissolved in a solvent and is treated with nicotinic acid or activated form of nicotinic acid such as nicotinoyl chloride or corresponding anhydride in presence of a base and optionally with a catalyst and/or a dehydrating agent at a temperature in the range of 0 to 60° C.

The active pharmaceutical ingredient as utilized herein may be selected from paclitaxel, docetaxel, cabazitaxel, tadalafil, curcumin. The base may be selected from any base such as DIPEA (N,N-Diisopropylethylamine), triethylamine or pyridine or an inorganic base such NaH (sodium hydride) or carbonate salt of sodium or potassium. The solvent may be selected from dichloromethane, tetrahydrofuran, acetonitrile, ethyl acetate, dimethylformamide etc. The dehydrating agent may be N,N'-Dicyclohexylcarbodiimide or EDCI (please spell out the chemical name) etc with or without any co-catalyst such as dimethylaminopyridine.

Step 2: Synthesis of Compound of Formula I.

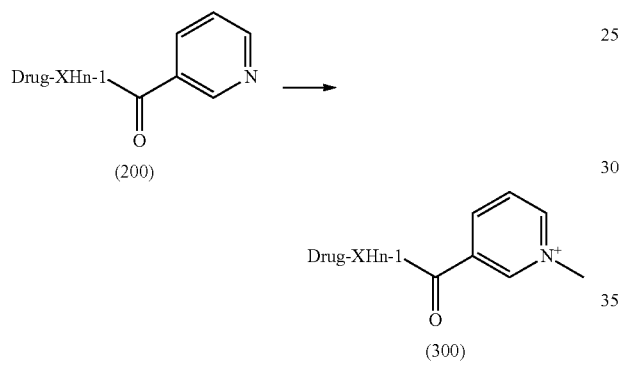

To the product of Step 1 in a suitable solvent is added alkyl halide such as MeI in stoichiometric or excess amount. The reaction is then stirred at a temperature in the range of 0° C. to refluxing for a period until maximum consumption of starting material. The solvent is removed under vacuum and the residue obtained is purified with solvent washing or crystallization to afford purified compound. The solvent may be selected from acetonitrile, ether, n-pentane, tetrahydrofuran.

In another embodiment, the process of the present invention may optionally comprise a co-catalyst such as tetrabutyl ammonium chloride, or other phase transfer catalyst, for example, quaternary ammonium salts, quaternary phosphonium salts, polyethylene glycols, crown ethers, alkyl sulfate salts, and alkyl sulfonates, can be exemplified amphoteric surfactants and the like, typically, tetrabutylammonium hydrogen sulfate, tetrabutylammonium bromide, tetrabutylammonium chloride, aliquots 336, hydrogen trioctylmethylammonium sulfate ammonium, 18-crown-6, tetrabutyl phosphonium chloride, sodium dodecylsulfate, although lauryl dimethylamino acetic acid betaine and the like, in addition they usable alone that alone, also be used as mixtures of two or more thereof it can.

Step 3:

Optionally, reacting an active pharmaceutical ingredient (API) of formula D-XHn with 3,3'-(oxybis(carbonyl))bis(1-methylpyridin-1-ium) iodide to obtain compound (300)

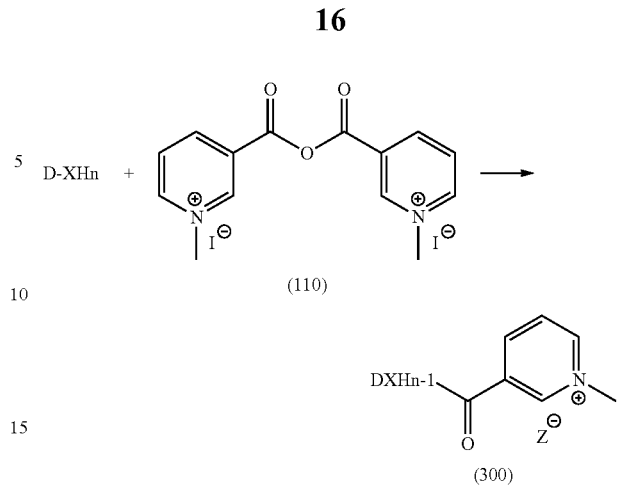

Step 4:

Optionally, converting the iodide counter ion of compound (300) to another counter ion by adding a catalyst and appropriate counter ion to obtain the compound (400)

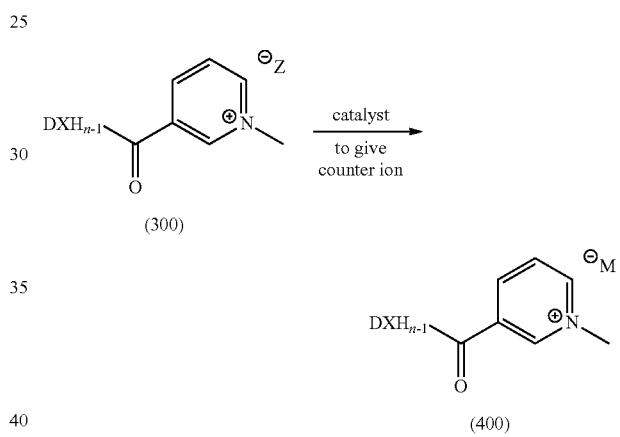

Wherein $M^{\ominus}$ is any counter ion selected from iodide, chloride, bromide, mesylate, tosylate or tetra flouroborate or any other pharmaceutically acceptable anion and the counter ion is either one or more counter ions to balance the charge The modified pharmaceutical compounds of the present invention have enhanced pharmacokinetic properties as compared to active pharmaceutical ingredient. The modified drugs have more solubility in wide pH ranges. The modified compounds of the present invention have a desirable safety and toxicity profile. The modified compounds of the present invention dissociate into the pharmaceutical compound and a compound of formula IV in the body.

Formula IV

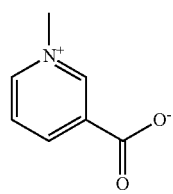

The compound of Formula IV is generically known as Trigonelline. Trigonelline (N-methylnicotinate) is a pyridine alkaloid with chemical formula $C_7H_7NO_2$ mostly reported from family Fabaceae. It is generally found in the seeds of the plant, *Trigonella foenum-graecum*, which is also known as Fenugreek or Methi. It is a zwitterion formed by the methylation of the nitrogen atom of niacin (vitamin $B_3$). It is a hypocholesterolemic agent and has nutritional benefits and glucose lowering activity.

Trigonelline has a GRAS (Generally Recognized as Safe) status by the FDA. Since it is a naturally occurring metabolite found in the plants, it is believed that the body is better able to process the new molecule back into the active, parent drug.

The modified compounds of this invention are suitable for use as drugs and/or pharmaceutical agents with improved pharmacokinetic property, while maintaining a desirable safety and toxicity profile. The invention also provides a method of alteration of pharmacokinetic profile of the compounds to render them more soluble in saline and/or at biologically useful pHs.

The novel compounds of the present invention may be used for pharmaceutical and neutraceutical purposes. The compounds of the present invention are used to treat different types of cancers, including lymphoma and cancers of the head and neck, breast, esophagus, lungs, stomach, bladder, prostate, ovarian, melanoma and other types of solid tumors; Kaposi's sarcoma; in the treatment of inflammatory disorders such as skin disorders: acne vulgaris, pulmonary arterial hypertension, anxiety, Alzheimer's disease, apoptosis; erectile dysfunction; severe hypotension, bradycardia (slow heart rate), circulatory shock, or cardiac arrest.

The present invention includes within its scope the salts, solvates and isomers. Solvates of the compounds of formula I and formula VI are preferably hydrates or any other pharmaceutically acceptable solvate.

All stereoisomers of the present compounds, such as those which may exist due to asymmetric carbons on the active pharmaceutical ingredient or the drug substance, including enantiomeric and diastereomeric forms, are contemplated within the scope of this invention. Individual stereoisomers of the compounds of the invention may, for example, be substantially free of other isomers, or may be admixed, for example, as racemates or with all other, selected, stereoisomers. The chiral centers of the present invention can have the S or R configuration.

The present invention also envisages within its scope the effect of selection of suitable counter ions. The counter ion of the compounds of the present invention may be chosen by selecting the dissociation constant for the drug capable of ionization within the said pH range. The counter anions are selected from halides, mesylates, tosylates, borates, carbonates, phosphates etc.

The invention thus also provides the use of the modified entity as defined herein for use in human or veterinary medicine. The compound for use as a pharmaceutical may be presented as a pharmaceutical formulation.

The invention therefore provides in a further aspect a pharmaceutical formulation comprising the modified compounds of the invention with a pharmaceutically acceptable carrier thereof and optionally other therapeutic and/or prophylactic ingredients. The carriers must be "acceptable" in the sense of being compatible with the other ingredients of the formula and not deleterious to the recipient thereof. Suitably the pharmaceutical formulation will be in an appropriate unit dosage form.

The pharmaceutical formulations may be any formulation and include those suitable for oral, intranasal, intraocular or parenteral (including intramuscular and intravenous) administration. The formulations may, where appropriate, be conveniently presented in discrete dosage units and may be prepared by any of the methods well known in the art of pharmacy. All methods include the step of bringing into association the active compound with liquid carriers or finely divided solid carriers or both, and then, if necessary, shaping the product into the desired formulation.

Without being limited by theory, the compounds of the present invention may not be suitable substrates or inhibitors of the cytochrome P450 enzymes, such as CYP3A4, enabling reduction in dose of the active pharmaceutical ingredient or the drug substance and increasing the safety and efficacy.

For these purposes the compounds of the present invention may be administered orally, topically, intranasal, intraocularly, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasteral injection or infusion techniques. In addition to the treatment of warm-blooded animals such as mice, rats; horses, dogs, cats, etc., the compounds of the invention are effective in the treatment of humans

EXAMPLES

The following examples are representative of the disclosure, and provide detailed methods for preparing the compounds of the disclosure, including the preparation of the intermediate compounds. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions.

As used herein the symbols and conventions used in these process, schemes and examples, regardless of whether a particular abbreviation is specifically defined, are consistent with those used in the contemporary scientific literature, for example, the Journal of American Chemical Society or the Journal of Biological Chemistry.

Example 1: Synthesis of Compound 1001 of Formula I
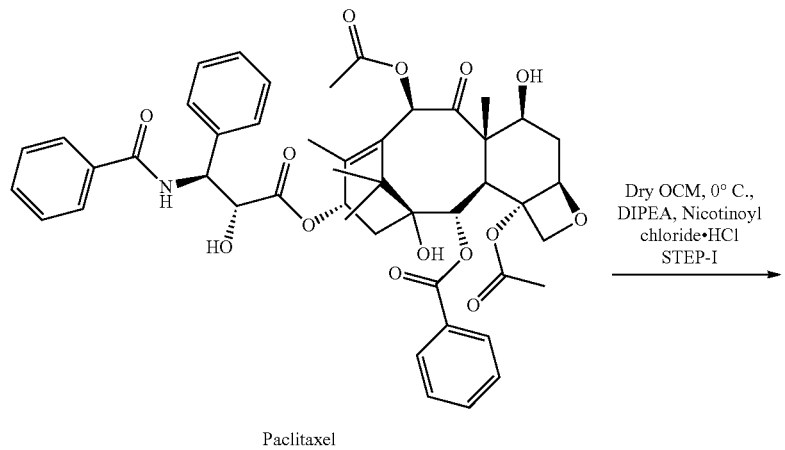
Paclitaxel
Dry DCM, 0° C., DIPEA, Nicotinoyl chloride•HCl
STEP-I →
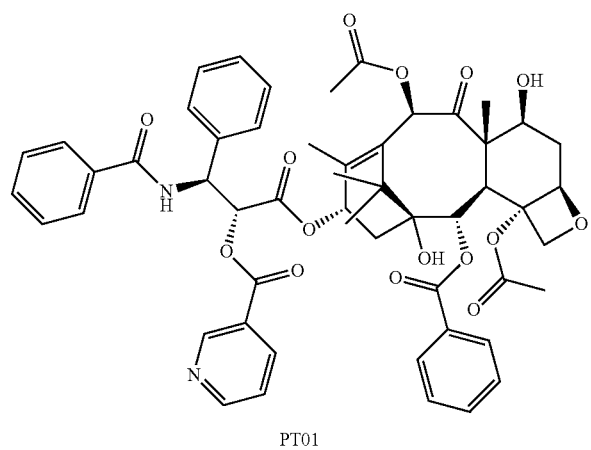
PT01
ACN, RT, MeI (large excess)
STEP-II →
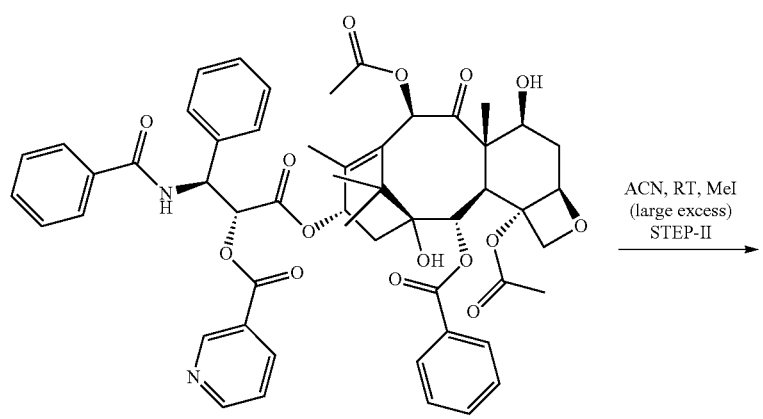

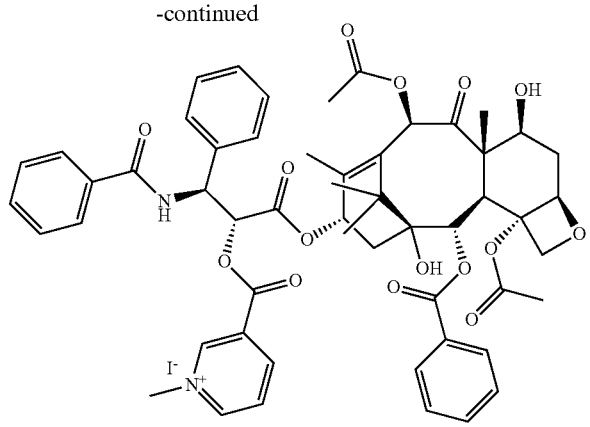

Synthesis of 2'-Nicotinate Ester of Paclitaxel:

Step-1:

To a solution of Paclitaxel [1.0 g, 1.1709 mmol, 1.0 mol eq] in dry DCM 25 ml under nitrogen atmosphere, at 0° C. was added DIPEA [0.755 g, d=0.756, 5.8527 mmol, 5.0 eq] and the reaction stirred for 15 min at the same temperature. To the above reaction was added Nicotinoyl chloride hydrochloride salt [0.625 g, 3.0 eq] all at once, while maintaining the temperature 0° C. The reaction was stirred at 0° C. for another 30 min and at RT for 24 h. The reaction was worked-up by treating the reaction mass with 5% aqueous HCl 2×20 ml, followed by water 2×20 ml, drying over anhydrous Na$_2$SO$_4$ and removing the solvent under vacuum to get the desired product. Yield: 89%.

MS: m/z at 959 and 960,

Step-2:

Synthesis of Trigonelline Ester:

To a solution of 2'-Nicotinate ester of Paclitaxel [0.03 g, 0.03125 mmol] in dry ACN 5 ml at RT was added Methyl Iodide in large excess [0.5 ml]. The reaction was stirred at RT for 24 h. ACN was removed under vacuum and the yellow residue is treated with 1:1 mixture of pentane/diethyl ether 5 ml and triturated to get free flowing yellow-brown crystals. This process yields the final product 1001 and yield is ~60%.

Examples 2-4: Synthesis of Compound (1002), Compound (1003) and Compound (1004) is Done Exploiting Procedure of Synthetic Example 1 Above

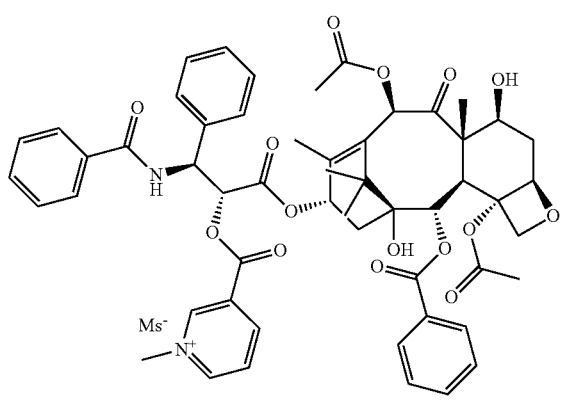

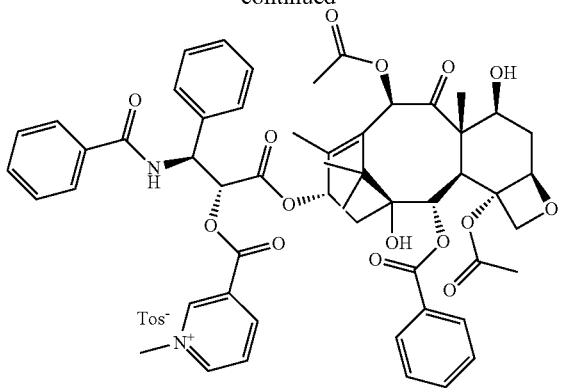

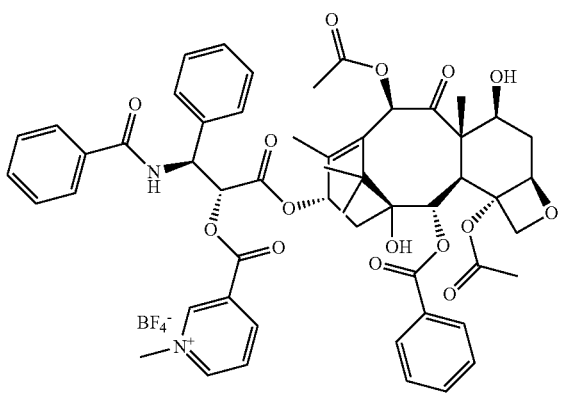

MS: m/z 974, 975 and 976

The iodide counterion is converted to the mesylate ion by adding silver(I) methanesulfonate (1.0 eq) at RT. The reaction mixture was stirred at RT for 2 h. The reaction was filtered to remove silver iodide. Filtrate was concentrated under vacuum, which was triturated with dry ether (2×5 ml), ether removed by decantation and product dried under vacuum to get the desired product mesylate. This process yields the final product [1002], [1003], [1004] mesylate as the desired product mesylate.

The above procedure is used to synthesize a derivative of curcumine compound (1006) and compound (1007), docetaxel (1008) and Gemcitabine (1009) and compound (1010) as below:

23

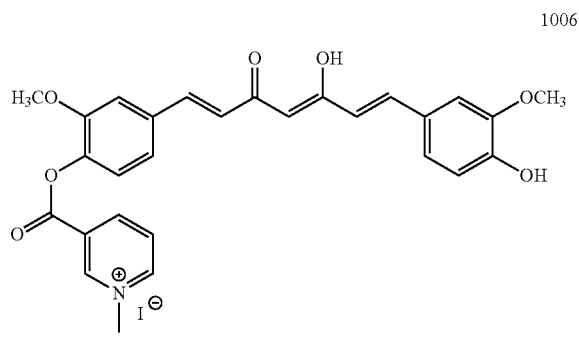

1006

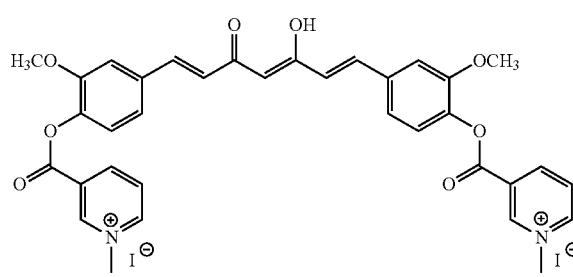

1007

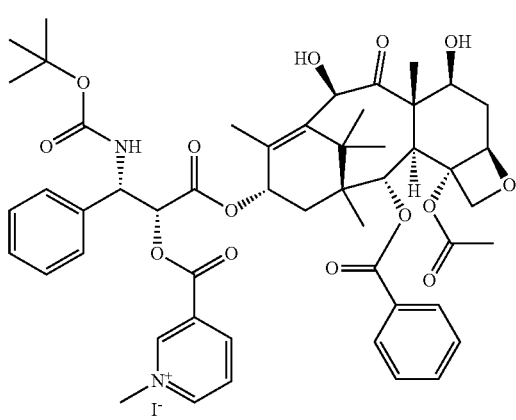

1008

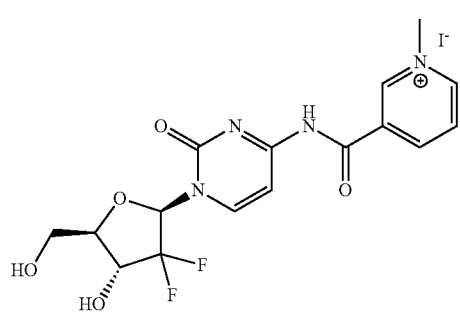

1009

24

-continued

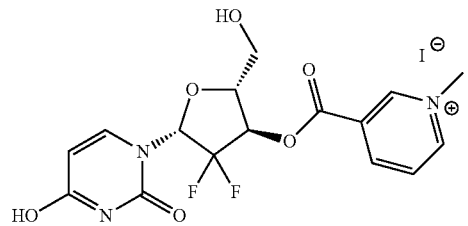

1010

Example 5: Synthesis of 3-((6R,12aR)-6-(benzo[d][1,3]dioxol-5-yl)-2-methyl-1,4-dioxo-1,2,3,4,6,7,12,12a-octahydropyrazino[1',2':1,6]pyrido[3,4-b]indole-7-carbonyl)-1-methylpyridin-1-ium iodide Compound (1005)

Step 1: Synthesis of (6R,12aR)-6-(benzo[d][1,3]dioxol-5-yl)-2-methyl-7-nicotinoyl-2,3,6,7,12,12a-hexahydropyrazino[1',2':1,6]pyrido[3,4-b]indole-1,4-dione

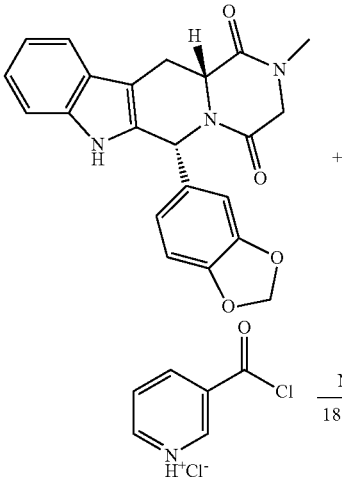

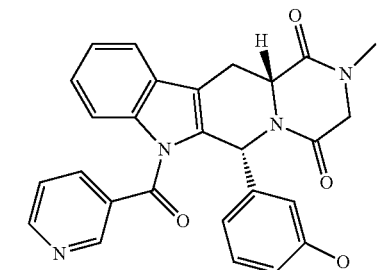

To a solution of tadalafil [0.05 g, 0.128 mmol] in dry THF at 0° C. was added NaH [0.020 g, 0.257 mmol, 2.0 eq] and reaction stirred until turned to yellow; another portion of NaH [0.020 g, 0.257 mmol, 2.0 eq] was added followed by addition of nicotinoyl chloride hydrochloride [0.045, 0.257, 2.0 eq] at 0° C. The reaction was stirred for another 1 h at 0° C. and then at 30° C. for 30 min, followed by addition of catalytic amounts of 18-crown-6. The reaction was heated to 55° C. (external) and reaction stirred for 36 h. The reaction was poured in water and extracted with ethyl acetate 10 ml×2 times, dried and ethyl acetate removed under vacuum to get yellow product. Yield 38 mg. m/z at 494

Step 2: Synthesis of 3-((6R,12aR)-6-(benzo[d][1,3]dioxol-5-yl)-2-methyl-1,4-dioxo-1,2,3,4,6,7,12,12a-octahydropyrazino[1',2':1,6]pyrido[3,4-b]indole-7-carbonyl)-1-methylpyridin-1-ium Iodide

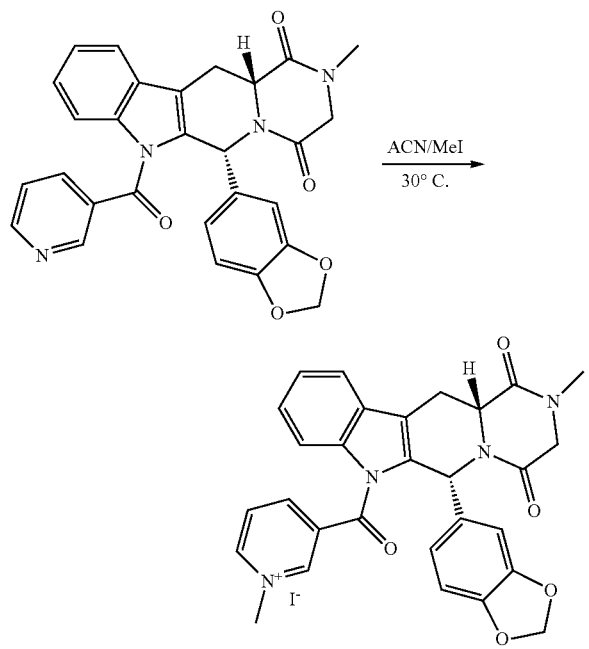

To a solution of 6R,12aR)-6-(benzo[d][1,3]dioxol-5-yl)-2-methyl-7-nicotinoyl-2,3,6,7,12,12a-hexahydropyrazino[1',2':1,6]pyrido [3,4-b]indole-1,4-dione [0.038 g] in dry ACN at 30° C. was added MeI [0.5 ml]. The reaction was stirred at the given temperature for 24 h. ACN was removed under vacuum, 1:1 ether:n-pentane added and triturated to get a yellow precipitate, which was isolated by filtration under suction and drying. This process yields the final product 1005 and yield is 10 mg. m/z at 509.

Example 6: Synthesis of 33-((R)-2-((S)-(2,8-bis(trifluoromethyl)quinolin-4-yl)(hydroxy)methyl)piperidine-1-carbonyl)-1-methylpyridin-1-ium Iodide (1011)

Step 1: Synthesis of ((R)-2-((S)-(2,8-bis(trifluoromethyl)quinolin-4-yl)(hydroxy)methyl)piperidin-1-yl)(pyridin-3-yl)methanone

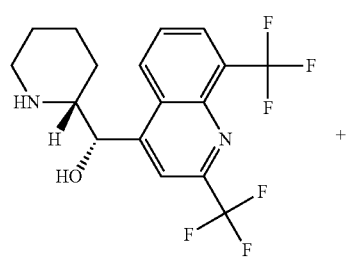

+

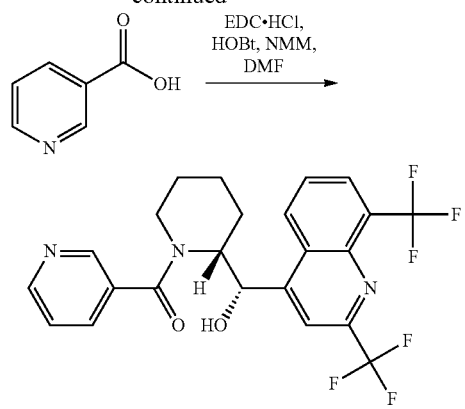

To a solution of Mefloquine[0.150 g, 0.39 mmol, 1 eq] in DMF 2 ml was added EDC [0.090 g, 0.47 mmol, 1.2 eq] and HOBt [0.069 g, 0.51 mmol, 1.3 eq] then stirred at RT for 20 mins. Now NMM [0.1 ml, 0.79 mmol, 2 eq] and nicotinic acid [0.058 g, 0.47 mmol, 1.2 eq] then stirred at RT for 24 hr. Ice cold water was slowly added in to the reaction mass, solid so formed was filtered and washed with cold water and dried over vacuum to obtain ((R)-2-((S)-(2,8-bis(trifluoromethyl)quinolin-4-yl)(hydroxy)methyl)piperidin-1-yl)(pyridin-3-yl)methanone (Yield; 0.100 g, 67%). m/z at 484

Step 2: Synthesis of 33-((R)-2-((S)-(2,8-bis(trifluoromethyl)quinolin-4-yl)(hydroxy)methyl)piperidine-1-carbonyl)-1-methylpyridin-1-ium Iodide

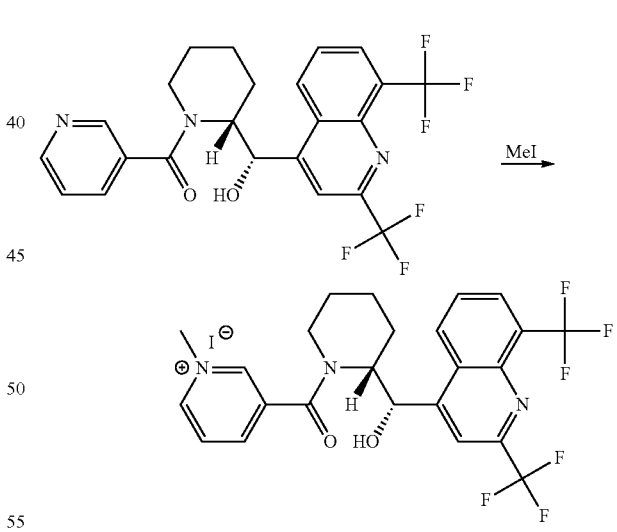

To a solution of ((R)-2-((S)-(2,8-bis(trifluoromethyl)quinolin-4-yl)(hydroxy)methyl)piperidin-1-yl)(pyridin-3-yl)methanone [0.050 g] was added MeI [0.1 ml]. The reaction was stirred at the given temperature for 24 h. Reaction mass was evaporated under vacuum, 1:1 ether:n-pentane added and triturated to get a brown solid 33-((R)-2-((S)-(2,8-bis(trifluoromethyl)quinolin-4-yl)(hydroxy)methyl)piperidine-1-carbonyl)-1-methylpyridin-1-ium iodide. This process yields the final product 1011 and yield is 0.035 g, 70%). m/z at 498.

Example 7: Evaluation of Solubility Profile of the Compounds of the Present Invention 1 mg/ml and 2 mg/ml solution of Mefloquine and Tadlafil respectively and equivalent weight of respective trigonelline modified compound (1011), compound (1005) of the present invention was taken in miliQ water, vortexed, centrifuged for 3 min, filtered and loaded on HPLC column (Zorbax Eclipse C18; Mobile Phase: A: 0.1% TFA, B: ACN; run time 15 min, Waters 2996 HPLC model). Area under the curve for each was determined and based on that fold increase in solubility was determined The results are presented herein below at Table 2.

TABLE 2

Solubility profile of the compounds of the present invention

| Compound | RT | Solubility | Concentration used for HPLC analysis | Fold increase in solubility for equiv. wt of DM using HPLC |
|---|---|---|---|---|
| Mefloquine | 6.92 | Poor solubility | 1 mg/ml | — |
| 1011 | 7.03 | Completely soluble | 1 mg/ml | 2.4 fold increase |
| Tadalafil | 7.13 | Very poor solubility | 2 mg/ml | — |
| 1005 | 5.93 | Completely soluble | 2 mg/ml | 80 fold increase |

As shown above in table 2, both modified compound (1011) and compound (1005) of the present invention showed significant increase in aqueous solubility over their parent drugs.

Example 8: Solubility of Paclitaxel Modified Drug (1001)

Trigonelline modified drug of Paclitaxel (1001) was evaluated for its aqueous solubility. Solubility was checked in different solvent systems. Only those solvents were selected which were found to solubilize the modified drug at the desirable concentrations and maintains the stability of the molecule. Modified drugs were found to be stable in the selected solvents.

Solubility of modified drug (1001) was evaluated in normal saline, 5% DMA in normal saline, 9% NMP in normal saline and 5% DMSO in normal saline.

Paclitaxel and compound (1001) presented in the present invention was taken in different solvent systems mentioned above, vortexed, centrifuged for 3 min, filtered and loaded on HPLC column (Zorbax Eclipse C18); Waters 2996 HPLC model). Area under the curve for each were determined and based on that fold increase in solubility was determined. The results are presented herein below at Table 3.

TABLE 3

Solubility results of Paclitaxel and compound 1001

| Compound | Normal saline | 5% DMA in normal saline | 9% NP in Normal Saline | 5% DMSO in Normal saline |
|---|---|---|---|---|
| Paclitaxel | 0.1 ug/ml | Not soluble | Not soluble | Not soluble |
| 1001 | >500 ug/ml | ~1 mg/ml | >1.5 mg/ml | >1.2 mg/ml |

Fold increase in solubility:
>5000× in Normal Saline
>10,000× in Normal Saline with 5% Dimethylacetamide
>12,000× in Normal Saline with 5% Dimethylsulfoxide
>15,000× in Normal Saline with 9% N-Methylpyrrolidone From Table 3 above, it can be seen that the compound (1001) of the present invention demonstrate increased solubility.

Example 9: Comparative PK Profile of Paclitaxel Modified Drug (1001) with Parent Drug Paclitaxel Pharmacokinetics studies were carried out to evaluate the plasma exposure of modified drug of Paclitaxel in SD rats when dosed intravenously (IV). The results were compared with exposure of Paclitaxel using the same dosing vehicle. The dosing vehicle that was used in this study was PEG400 and Normal saline in fixed composition. The compound of the present invention (1001) was found to be stable and soluble in the given solvent. As reported in solubility data, (1001) displayed better aqueous solubility. This resulted in easier IV dosing in case of modified drugs. 3 mpk and 1 mpk IV dosing was done for the modified drug and 3 mpk IV for Paclitaxel parent drug. After IV dosing of the modified drug blood was collected by serial bleeding at different time points in heparinized tubes. Blood samples were centrifuged at 10,000 rpm for 5 min at 4° C. to obtain the plasma, which were aspirated into separate labeled tubes and stored at −80° C. Extraction solvent was added to plasma, was vortexed and shaken on shaker for 10 minutes, centrifuged at 10,000 rpm for 10 minutes at 4° C. Supernatant was kept for analysis.

Acetonitrile and plasma calibration curves were generated and percentage of drug recovery from plasma determined Quantitative analysis was done by liquid chromatography tandem mass spectrometer (API3000 LC-MS/MS). Cmax, Tmax, AUC and t½ were calculated using Graph Pad PRISM version 5.04 and the results are depicted in Table 4

TABLE 4

Pharmacokinetic profile of the compounds of the present invention (Paclitaxel)

| Formulation | Compound | Dose (mg/Kg, iv) | $T_{1/2}$ (hr) | $C_{max}$ (nm) | AUC (nM * hr) |
|---|---|---|---|---|---|
| PEG/Normal Saline | Paclitaxel | 3 | 2.5 | 104 | 67 |
| | 1001 | 3* | 0.6 | 8620 | 874 |
| | 1001 | 1* | 1.2 | 2384 | 301 |

*3 mpk 1001 = 2.1 mpk Paclitaxel delivered
*1 mpk 1001 = 0.71 mpk Paclitaxel delivered It can be seen from Table 4 that the modified compound (1001) of the present invention has more than 80 folds increase in the Cmax and more than 10 fold increase in the AUC. Hence, the compounds (1001) of the present invention have increased pharmacokinetic and solubility over the API compounds.

Example 10: Pharmacokinetic Profile of the Compounds (1008) of the Present Invention (Docetaxel)

Pharmacokinetics studies were carried out to evaluate the plasma exposure of modified drug of Docetaxel (1008) in SD rats when dosed intravenously (IV). The results were compared with exposure of Docetaxel (10 mpk) using the same dosing vehicle. The dosing vehicle that was used in this study was PEG400 and Normal saline in fixed composition. Modified drug of Docetaxel (1008) was found to be stable and soluble in the given solvent.

Docetaxel modified drug (1008) was found to have significantly higher exposure as compared to the parent drug as shown in table As reported in solubility data, modified drug of Docetaxel (1008) displayed better aqueous solubility. 3 mpk IV dosing was done for the modified drug (1008) and 10 mpk IV for Docetaxel parent drug. After IV dosing of the modified drug blood was collected by serial bleeding at different time points in heparinized tubes. Blood samples were centrifuged at 10,000 rpm for 5 min. at 4° C. to obtain the plasma, which were aspirated into separate labeled tubes and stored at −80° C. Extraction solvent was added to plasma, was vortexed and shaken on shaker for 10 minutes, centrifuged at 10,000 rpm for 10 minutes at 4° C. Supernatant was kept for analysis.

Acetonitrile and plasma calibration curves were generated and percentage of drug recovery from plasma determined Quantitative analysis was done by liquid chromatography tandem mass spectrometer (API3000 LC-MS/MS). Cmax, Tmax, AUC and t½ were calculated using Graph Pad PRISM version 5.04 and the results are depicted in Table 5

TABLE 5

Pharmacokinetic profile of the compounds (1008) of the present invention

| Parameters | Docetaxel 10 mpk IV | 1008 |
| --- | --- | --- |
| Cmax (nM) | 494.96 | 6924.21 |
| Tmax (hr) | 0.08 | 0.08 |
| AUC (nM * hr) | 897.47 | 1035.34 |
| $T_{1/2}$ elimination (hr) | 2.06 | 1.78 |

From table 5 above, it can be seen that the compound (1008) of the present invention has enhanced pharmacokinetics than the original compound.

The invention claimed is:

1. A compound according to Formula I with improved solubility and altered pharmacokinetic properties

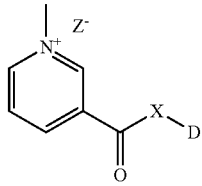

Formula I wherein DX— is an active pharmaceutical ingredient (API) or a drug substance and;
X is either O, or NR;
Z is Cl—, Br—, I—, mesylate, tosylate, tetrafluoroborate, carbonate or phosphate;
R is H, CH₃, lower straight chain or branched chain alkyl, alternatively X can also be part of a 3-7 membered ring when there is a bond present between R and another atom on D, wherein the compound is selected from
i. 3-((((1R,2R)-1-benzamido-3-(((2aR,4S,6R,9S,11Si 2S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium iodide;
ii. 3-((((1R,2R)-1-benzamido-3-(((2aR,4S,6R,9S,11Si 2S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Mesylate;
iii. 3-((((1R,2R)-1-benzamido-3-(((2aR,4S,6R,9S,11Si 2S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tetrafluoroborate;
iv. 3-((((1R,2R)-1-benzamido-3-(((2aR,4S,6R,9S,11Si 2S,12bS)-6,12b-diacetoxy-12-(benzoyloxy)-4,11-dihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-oxo-1-phenylpropan-2-yl)oxy)carbonyl)-1-methylpyridin-1-ium Tosylate;
v. 3-((6R,12aR)-6-(benzo[d][1,3]dioxol-5-yl)-2-methyl-1,4-dioxo-1,2,3,4,6,7,12,12a-octahydropyrazino[1',2'1,6]pyrido[3,4-b]indole-7-carbonyl)-1-methylpyridin-1-ium iodide;
vi. 3-((4-((1E,4Z,6E)-5-hydroxy-7-(4-hydroxy-3-methoxyphenyl)-3-oxohepta-1,4,6-trien-1-yl)-2-methoxyphenoxy)carbonyl)-1-methylpyridin-1-ium iodide;
vii. 3,3'-(((((1E,3Z,6E)-3-hydroxy-5-oxohepta-1,3,6-triene-1,7-diyl)bis(2-methoxy-4,1-phenylene))bis(oxy))bis(carbonyl))bis(1-methylpyridin-1-ium) iodide;
viii. 3-((((2R,3S)-1-(((2aR,4S,4aS,6R,9S,11S,12S,12aR,12bS)-12b-acetoxy-12-(benzoyloxy)-4,6,11-trihydroxy-4a,8,13,13-tetramethyl-5-oxo-2a,3,4,4a,5,6,9,10,11,12,12a,12b-dodecahydro-1H-7,11-methanocyclodeca[3,4]benzo[1,2-b]oxet-9-yl)oxy)-3-((tert-butoxycarbonyl)amino)-1-oxo-3-phenylpropan-2-yl)oxy)carbonyl)-1-methylpyridin-1-ium iodide;
ix. 3-((1-((2R,4R,5R)-3,3-difluoro-4-hydroxy-5-(hydroxymethyl)tetrahydrofuran-2-yl)-2-oxo-1,2-dihydropyrimidin-4-yl)carbamoyl)-1-methylpyridin-1-ium iodide;
x. 3-((((2R,3R,5R)-5-(4-amino-2-oxopyrimidin-1(2H)-yl)-4,4-difluoro-2-(hydroxymethyl)tetrahydrofuran-3-yl)oxy)carbonyl)-1-methylpyridin-1-ium iodide;
xi. 3-((R)-2-((S)-(2,8-bis(trifluoromethyl)quinolin-4-yl)(hydroxy)methyl)piperidine-1-carbonyl)-1-methyl-pyridin-1-ium;
xii. (R)-3-(((1-(4-((2-(5-chloro-2-fluorophenyl)-5-isopropylpyrimidin-4-yl)amino)nicotinamido)propan-2-yl)oxy)carbonyl)-1-methylpyrin-1-ium; and
xiii. (S)-3-(((1-(4-((2-(5-chloro-2-fluorophenyl)-5-isopropylpyrimidin-4-yl)amino)nicotinamido)propan-2-yl)oxy)carbonyl)-1-methylpyrin-1-ium iodide.

2. The compound of claim 1, wherein the compound is not a substrate for CYP450.

* * * * *